United States Patent [19]
Yeh et al.

[11] Patent Number: 5,230,896
[45] Date of Patent: Jul. 27, 1993

[54] TRANSDERMAL NICOTINE DELIVERY SYSTEM

[75] Inventors: Sharlin E. Yeh, Randolph; Niranjan Patel, Dover; Josephine Milstone, Ridgefield Park, all of N.J.

[73] Assignee: Warner-Lambert Company, Morris Plains, N.J.

[21] Appl. No.: 420,963

[22] Filed: Oct. 12, 1989

[51] Int. Cl.$^5$ .............................................. A61F 13/00
[52] U.S. Cl. ................................... 424/443; 424/448; 424/449; 427/303.1
[58] Field of Search ............... 424/447, 448, 449, 443; 427/303.1

[56] References Cited

U.S. PATENT DOCUMENTS

| | | | |
|---|---|---|---|
| 3,598,122 | 8/1971 | Zaffaroni | 128/268 |
| 3,731,683 | 5/1973 | Zaffaroni | 128/268 |
| 4,597,961 | 7/1986 | Etscorn | 424/28 |
| 4,624,665 | 11/1986 | Nuwayser | 604/307 |
| 4,655,768 | 4/1987 | Marecki et al. | 604/897 |
| 4,675,009 | 6/1987 | Hymes et al. | 604/304 |
| 4,710,191 | 12/1987 | Kwiatek et al. | 604/897 |
| 4,743,249 | 5/1988 | Loveland | 424/447 |
| 4,822,617 | 4/1989 | Panoz | 424/449 |
| 4,834,978 | 5/1989 | Nuwayser | 424/448 |
| 4,839,174 | 6/1989 | Baker et al. | 424/447 |
| 4,877,618 | 10/1989 | Reed, Jr. | 424/448 |
| 4,880,633 | 11/1989 | Loper et al. | 424/449 |
| 4,946,853 | 8/1990 | Bannon et al. | 424/448 |

FOREIGN PATENT DOCUMENTS 60-94209 11/1986 Japan .

*Primary Examiner*—Thurman K. Page
*Assistant Examiner*—Leon R. Horne
*Attorney, Agent, or Firm*—Richard S. Bullitt

[57] ABSTRACT

A novel transdermal delivery system for nicotine to satisfy addicted smokers' cravings therefore is comprised of a nicotine base, an acrylate polymer adhesive, a stabilizer and a polyester film backing. The nicotine is absorbed through the skin at sufficiently high levels to reduce or eliminate the desire to smoke, yet its concentration within the acrylate matrix is such that a laminar patch is constructed that is neither bulky nor obvious when worn. A method of manufacture of the transdermal system is also described.

33 Claims, No Drawings

TRANSDERMAL NICOTINE DELIVERY SYSTEM

BACKGROUND OF THE INVENTION

Perhaps some of the most important medical issues for years has been the health risks associated with cigarette smoking such as lung cancer, heart disease and emphysema, just to name a few. Moreover, new medical evidence regarding the dangers of exposure to second hand smoke by non-smokers has resulted in a societal conflict between the rights of smokers and those of the non-smoker. Despite attempts by many smokers to quit for both health reasons and peer pressure, their addiction to the nicotine element of cigarette smoke prevents their doing so as they have become both physiologically and psychologically dependant.

Hence, numerous products have been developed in the past to administer nicotine in a manner other than cigarette smoke so as to cure the craving while at the same time avoiding the deleterious effects of tars and carbon monoxide, inherent components of cigarette smoke. Nicotine containing pills have been developed, see U.S. Pat. No. 3,368,567 to Speer, however these have failed to successfully quell the nicotine craving since they are unable to achieve effectively high nicotine blood levels. A drug such as nicotine that is administered orally and absorbed by the stomach must first pass through the liver where most of it is deactivated. Nicotine-containing chewing gum encounters much of the same deactivation problems although some have found modest market success such as Nicorette®, Lakeside Pharmaceuticals, Cincinnati, Ohio. These have also raised concerns regarding the causation of gum disease and their less than pleasant taste also affects patient compliance.

The object of the present invention is to provide a means, both economically and conveniently, for the administration of nicotine to the bloodstream of an addicted cigarette smoker by a means that will both avoid nicotine deactivation by the liver and will result in nicotine blood concentrations that will sufficiently satisfy the cravings of even the most ardent nicotine-dependant cigarette smoker. It is a further object of the present invention to provide a small, thin layered patch for the transdermal administration of nicotine to the blood stream in amounts sufficiently high enough to quell any craving for the drug so as to lessen or avoid any psychological or physiological discomfort by the addicted cigarette smoker. It is a further object of the present invention to provide a transdermal delivery system for nicotine composed of thin layered patches containing a range of concentrations of nicotine contained therein so that a gradual withdrawal from the substance can occur over time resulting in an eventually complete elimination of the addiction. Finally, it is an object of the present invention to provide a thin layered transdermal patch that can be discretely worn by the addict and yet contain sufficiently high concentrations of nicotine so as to be effective in reducing the addict's craving therefore.

The transdermal delivery of a drug to the blood system is well known in the art and much research has been carried out in this field. Most of this technology involves incorporation of the drug of interest into a matrix or carrier solvent which is held in a reservoir formed by a drug-impermeable backing and a drug permeable membrane that is placed in contact with the skin and through which the drug diffuses. See U.S. Pat. Nos. 4,655,768 to Marecki et al; 4,710,191 to Kwiatek et al. and 4,624,665 to Nuwayser et al. The permeable membranes are comprised of biologically useful polymers such as vinyl pyrrolidone and allylamine cross-linked with glutaraldehyde ('484), ethylene vinyl acetate copolymer ('665) and other acrylic copolymers in general. Some membranes are microporous in nature and allow for the diffusion of the active agent as microparticles. See U.S. Pat. Nos. 3,731,683 and 3,598,122 to Zaffaroni et al. and U.S. Pat. No. 4,743,249 to Loveland.

Most of the transdermal drug delivery patches or bandages known in the art are directed towards a controlled release of the drug for a prolonged period of time and unfortunately, the skin serves as an effective barrier against the permeation of most drugs into the human body. Delivery systems using a carrier solvent in a reservoir containment for the drug provide a steady flux of the drug across the membrane so long as undissolved drug remains in the reservoir. Matrix transdermal systems invariably provide a decreasing delivery of the drug with time as layers closer to the skin become depleted of the drug and those still containing the active are farther away and diffuse more slowly. Moreover, the need for a reservoir type containment system is bulky and often obvious to any casual observer. As a result, despite much research in the field only nitroglycerin, scopolamine, clonidine and estradiol have been commercially exploited in the transdermal area.

U.S. Pat. No. 4,822,617 to Parroy does disclose a transdermal drug delivery device that does away with the reservoir concept, but here the drug such as nitroglycerin, scopolamine etc., is incorporated in a lanolin petroleum-based ointment which is then spread about the surface of a laminar applicator containing recesses for containment of the drug. There is no permeable membrane and the ointment itself adheres the device to the skin. A strip of adhesive may also be used for greater security. Whereas other transdermal drug delivery systems known in the art have approached thinner laminar dimensions, they all require a three component structure and often require both a solid and liquid dispersion of the active to be administered. See U.S. Pat. No. 4 675,009 to Hynes et al. It is also evident from the prior art patents that the membrane, matrix or solvent employed is dependant upon the active as well.

Nicotine is not known for any therapeutic value and hence it has only been recently that work has been done whereby nicotine is incorporated in a transdermal delivery system as an aid to quit smoking.

U.S. Pat. No. 4,597,961 to Etscorn entitled "Transcutaneous Application of Nicotine" discloses a transdermal patch comprised of an occlusive backing and a reservoir which contains the nicotine dissolved in a carrier or solvent and a microporous membrane for diffusion of the nicotine to the skin. The rate of diffusion is low however, and due to the structure of the membrane and the manner in which the nicotine diffuses through to contact the skin, many patches would have to be worn during the course of a day in order to reach and maintain nicotine plasma levels sufficiently high enough to eliminate the craving for cigarettes. Moreover, the need for the reservoir containment system results in a bulky patch that is readily apparent to the casual observer.

A more recent development in this area is disclosed in U.S. Pat. No. 4,839,174 to Baker et al. wherein a transdermal nicotine patch is described. The patch is comprised of an impermeable backing layer, a polyurethane matrix in which liquid nicotine is dispersed and an adhesive which holds the patch in contact with the skin. The matrix is comprised of a polyether type polyurethane that is dissolved in a solvent such as tetrahydrofuran (THF). The nicotine is added from 10-20% by weight and the mixture cured onto the impermeable backing layer in a thickness of from 50-800 microns, depending on the dosage of nicotine desired An amine-resistant bioadhesive layer is then added for attachment of the patch to the skin. Since nicotine is a very volatile substance, the curing step of the nicotine/polyurethane mixture onto the impermeable backing layer results in losses of up to 30% of the nicotine through degradation and/or evaporation. Therefore, the initial nicotine loading content must be substantially higher so as to make up for this loss and consequently the procedure is quite expensive when carried out on the commercial level.

Japanese Patent Application No. 60-94209 to Tsuda et al and assigned to the Nitto Electrical Industrial Co. also discloses a nicotine-containing tape preparation comprised of a macromolecular substance with nicotine (2-10% w/w) incorporated therein. Suitable macromolecular substances are silicone, polyisoprene, methylene-butadiene and acrylic rubbers as well as polyvinyl alkyl ethers, alcohols and acetates. The process for incorporating the nicotine active into the macromolecular substance requires dissolving it into an organic solvent such as ethyl alcohol or chloroform. The required use of these volatile materials raises environmental concerns resulting in increased costs of manufacture and also poses health risks by exposure of the manufacturers to the fumes. Moreover, it is doubtful whether the low (2-10% w/w) concentration of nicotine incorporated into the tape preparation is sufficiently high enough to achieve serum blood nicotine levels that will cure the craving of the addict.

SUMMARY OF THE INVENTION

The present invention is an improved transdermal delivery system for the controlled release of nicotine to the blood stream of those addicted to cigarette smoking. The improvement lies in the formulation whereby the nicotine is directly incorporated into the adhesive matrix thereby doing away with the need for bulky reservoir containments. The acrylic polymer adhesive matrix also surprisingly exerts a stabilizing effect on the nicotine compound which is inherently volatile.

DETAILED DESCRIPTION OF THE INVENTION

The transdermal delivery system of the present invention is an aid for smokers who, through their addiction to nicotine, are unable to refrain from subjecting their lungs to the noxious gases and tars found in cigarette smoke. The invention is based on the fact that human skin is essentially a permeable membrane and since certain chemical compounds can cross that barrier and are assimilated into the blood stream, the same can be done with nicotine. By raising the blood concentration of nicotine to a particular level, the psychological and physiological craving for it will subside and with proper use over a period of time will be eliminated altogether.

The instability of nicotine poses particular problems for its use as an active in a transdermal type delivery system. It is difficult to insure that any composition can contain sufficiently high enough concentrations of nicotine so as to raise serum blood nicotine levels to that which will cure the addictive craving. Lower concentration in the matrix of most prior art delivery systems may improve its stability but this will be unable to impart a sufficient amount of the drug to the bloodstream. The term, nicotine free base refers to nicotine in its pure form as represented by the chemical formula:

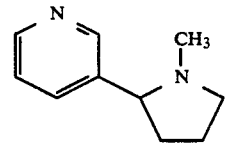

This is to be distinguished over the more soluble nicotine salt which may be formed by the addition of an acid as discussed infra. Both compounds are contemplated in the practice of the present invention.

The transdermal delivery system of the present invention then, comprises an adhesive matrix consisting of an acrylic polymer adhesive, a nicotine base and a stabilizer that is laminated onto an inert impermeable film backing.

The acrylic polymeric adhesive of the present invention is one of several related types. Preferably, it is comprised of a vinyl acetate-ethylene acrylate polymer commercially known as to Flexcryl TM manufactured by Air Products, Inc. of Allentown, Penna. This hydrous emulsion contains the polymer in ratios of from approximately 30-60% solids and can comprise anywhere from approximately 70-90% w/w of the adhesive-nicotine matrix composition. Other suitable acrylate polymers are available as organic solvents and are ethyl hexyl acrylate, butyl acrylate and ethyl acrylate. These are manufactured by National Starch Inc., Bridgewater, N.J. and The 3M Company, Minneapolis, Minn. The nicotine component comprises anywhere from approximately 10-20% w/w and this can be increased or decreased depending upon the severity of the addiction of the wearer. A stabilizing agent such as butylated hydroxytoluene comprises approximately 0.05-0.2% w/w of the final mixture. Other suitable stabilizing agents useful in the practice of the present invention are ascorbyl palmitate and ferrous oxide. In all instances, the resulting adhesive emulsion or organic adhesive solvent mixture is then dried onto an inert impermeable film or backing such as aluminum polyester or aluminum polyethylene polyvinyl acetate, also available from the 3M Company, Minneapolis, Minn.

In a preferred embodiment of the present invention, additional solvents such as water (approx. 3.0-7.0% w/w) and ethyl alcohol (USP) comprising approximately 3.0-6.0% w/w are employed to incorporate the stabilizer, an emulsion thickener and an acid. Whereas neither the acid nor the emulsion thickener are required components in the delivery system of the present invention, the presence of one requires the presence of the other. The emulsion thickener functions to firm up the nicotine acrylate matrix which upon the addition of water or organic solvent becomes quite viscous. Suitable thickeners are polyvinyl pyrrolidone, hydroxyethyl cellulose, hydroxypropyl methyl cellulose and mixtures thereof these can comprise from approximately 0.5-5.0% w/w of the adhesive matrix composition. Additionally, an acid such as L-tartaric acid, hydrochloric acid or salicylic acid may be added to the nicotine/acrylate adhesive formulation to further stabilize the nicotine free base, which is otherwise volatile, through the formation of a nicotine salt. The preferred embodiment of the present invention comprises an adhesive matrix of from about 60-75% w/w vinyl acetate-ethylene acrylate polymer, 15-20% w/w nicotine base, 4.0-10.0% w/w L-tartaric acid and 0.6-1.0% w/w emulsion thickener, approximately 0.1% w/w butylated hydroxytoluene as a stabilizer and an ethyl alcohol/water solvent in the aforementioned ratios.

Preferably, the acid, emulsion thickener and stabilizer are first dissolved in the water and ethyl alcohol (USP) respectively, and later added to the vinyl acetate/ethylene acrylate polymer to create a wet adhesive mixture. The nicotine component is subsequently incorporated and uniformly dispersed throughout by stirring, agitation or any one of the many methods known in the art. The matrix is spread over an inert impermeable backing such as aluminum polyester or aluminum polyethylene polyvinyl acetate and dried at 45°-55° C. to remove any excess water and alcohol until the surface is firm, dry and tacky. An impermeable inert silicone- or fluorocarbon-coated release liner is then laminated over the dry nicotine/polymer matrix in order to prevent the oxidation of nicotine during storage and/or any other reactions with the elements. This is then peeled off just prior to application to the skin.

The following examples are set forth herein for illustrative purposes only so as to better define and teach the practice of the present invention. They are for illustrative purposes only and are not to be construed as limiting either the spirit or scope of the invention as later recited in the claims.

EXAMPLE 1

The transdermal nicotine patch was prepared as follows. All weights are expressed as a percentage of the total weight of the composition. Nicotine free base (10.4% w/w) was homogeneously blended throughout a vinyl acetate-ethylene acrylate adhesive matrix (88.5% w/w). In a separate system, butyl hydroxytoluene (0.1% w/w) was dissolved in ethyl alcohol (USP) (1.0% w/w) and this solution was then mixed together with the nicotine/acrylate adhesive matrix. The viscous adhesive matrix was then spread upon an impermeable aluminum polyester film backing. The coated sheet was dried at approximately 45°-55° C. until firm yet sticky and a silicone-based release liner was then laminated over the exposed nicotine/acrylate polymer matrix. The laminated nicotine/acrylate sheet may then be cut to any desired shape and size, preferably a 1.0-1.5 inch diameter circle and packaged into moisture and oxygen impermeable packing material. When desired for use, the patch is removed from its package, the silicone-based release liner peeled away and the exposed nicotine/acrylate surface placed onto the skin.

EXAMPLE 2

In this preparation nicotine free base (19.8% w/w) was homogeneously blended throughout an ethyl hexyl acrylate polymer solution (79.1% w/w). In a separate blender, ascorbyl palmitate (0.1% w/w) was added as a stabilizer to ethyl alcohol (USP 1.0% w/w) and again the compounds are thoroughly mixed. The blend was combined with the nicotine/acrylate solution and spread about the backing of an aluminum-polyethylene polyvinyl acetate film. The nicotine adhesive matrix was dried at approximately 45°-55° C. and then laminated, cut and packaged as set forth in Example 1.

EXAMPLE 3

Nicotine free base (16.8% w/w) was blended with a butyl acrylate solution (67.2% w/w) until the nicotine was uniformly dispersed throughout. As in the previous examples, butyl hydroxytoluene (0.08% w/w) was dissolved in ethyl alcohol (USP 4.7% w/w) and held. To this mixture was added polyvinyl pyrrolidone (0.6% w/w) as a matrix thickening agent and in a separate system, L-tartaric acid (5.9% w/w) was dissolved in distilled (hot) water (4.7% w/w) and subsequently cooled to room temperature. The PVP/butyl hydroxytoluene/alcohol mixture was added to and thoroughly mixed with the nicotine/acrylate matrix. Once blended, the aqueous acid solution is added to the adhesive matrix and mixed. The formulation is spread about an aluminum polyester backing, dried as before and laminated with a second silicone-based release liner. The transdermal nicotine patches are cut in desired shapes and sizes and packaged as hereinbefore described.

The patches from Examples I-III were subjected to in-vitro permeation studies comparing their effectiveness with the patches of the prior art which have shown some clinical effectiveness. Using standard laboratory hairless mouse skin as the cutaneous substrate, the smaller, less bulky nicotine patches of the present invention showed permeation rates equivalent if not superior to those of the prior art.

What we claim is:

1. A transdermal delivery system for the subcutaneous administration of nicotine in an amount sufficient to reduce the craving therefore consisting essentially of an inert, impermeable film backing that supports an adhesive matrix comprising:
   a) an acrylic polymer adhesive,
   b) a nicotine base, and
   c) a stabilizer.

2. The transdermal delivery system of claim 1 wherein said acrylic polymer adhesive comprises approximately 70-90% of the total weight of the adhesive matrix formulation.

3. The transdermal delivery system of claim 2 wherein said acrylic polymer adhesive comprises approximately 85-90% of the total weight of the adhesive matrix formulation.

4. The transdermal delivery system of claim 2 wherein said acrylic polymer adhesive is selected from the group consisting of vinylacetate/ethylene acrylate, ethyl hexyl acrylate, butyl acrylate, ethyl acrylate and mixtures thereof.

5. The transdermal delivery system of claim 4 wherein said nicotine base comprises approximately 10-30% of the weight of said adhesive matrix formulation.

6. The transdermal delivery system of claim 5 wherein said nicotine base comprises approximately 10-15% by weight of said adhesive matrix formulation.

7. The transdermal delivery system of claim 5 wherein said nicotine base comprises approximately 15-20% by weight of said adhesive matrix formulation.

8. The transdermal delivery system of claim 5 wherein said stabilizer comprises approximately 0.05-0.2% by weight of said adhesive matrix formulation.

9. The transdermal delivery system of claim 8 wherein said stabilizer is selected from the group consisting of butylated hydroxytoluene, ascorbyl palmitate, ferrous oxide, and mixtures thereof.

10. The transdermal delivery system of claim 1 or 9 further comprising an emulsion thickener and an acid.

11. The transdermal delivery system of claim 10 wherein said emulsion thickener is selected from the group consisting of polyvinyl pyrrolidone, hydroxyethyl cellulose, hydroxypropyl methyl cellulose and mixtures thereof.

12. The transdermal delivery system of claim 11 wherein said thickener comprises approximately 0.3-1.5% by weight of said adhesive matrix formulation.

13. The transdermal delivery system of claim 10 wherein said acid is selected from the group consisting of L-tartaric acid, salicylic acid, hydrochloric acid and mixtures thereof.

14. The transdermal delivery system of claim 13 wherein said acid comprises 5.0-20.0% by weight of said adhesive matrix formulation.

15. The transdermal delivery system of claim 14 wherein said inert, impermeable film backing is selected from the group consisting of aluminum polyester and aluminum polyethylene polyvinyl acetate.

16. A method for the preparation of a transdermal delivery system for the subcutaneous administration of nicotine in an amount sufficient to reduce the craving therefore comprising:
   a) preparing an adhesive matrix consisting of an acrylic polymer adhesive, nicotine base, and a stabilizer,
   b) laminating said adhesive matrix onto an inert impermeable film backing,
   c) heating said adhesive matrix laminate at a sufficient temperature and time to evaporate any solvent contained therein and,
   d) laminating a removable release liner over the exposed surface of the dried acrylic adhesive/nicotine base matrix.

17. The method of claim 16 wherein said acrylic polymer adhesive comprises approximately 70-90% by weight of said adhesive matrix.

18. The method of claim 17 wherein said acrylic polymer adhesive is selected from the group consisting of vinyl acetate/ethylene acrylate, ethyl hexyl acrylate, butyl acrylate, ethyl acrylate and mixtures thereof.

19. The method of claim 18 wherein said nicotine base comprises approximately 10-30% by weight of said adhesive matrix.

20. The method of claim 19 wherein said nicotine base comprises approximately 15-20% by weight of said adhesive matrix.

21. The method of claim 20 wherein said stabilizer comprises approximately 0.05-2.0% by weight of said adhesive matrix.

22. The method of claim 21 wherein said stabilizer is selected from the group consisting of butylated hydroxytoluene, ascorbyl palmitate, ferrous oxide, and mixtures thereof.

23. The method of claim 22 wherein said inert, impermeable film backing is selected from the group comprising aluminum polyester and aluminum polyethylene polyvinyl acetate.

24. The method of claim 23 wherein said adhesive matrix laminate is heated to a temperature of approximately 40°-60° C.

25. The method of claim 24 wherein said release liner is silicone- or fluorocarbon-based.

26. The method of claim 1 wherein said emulsion thickener is selected from the group consisting of polyvinyl pyrrolidone, hydroxyethyl cellulose, hydroxy propyl methyl cellulose and mixtures thereof.

27. The method of claim 26 wherein said thickener comprises approximately 0.5-5.0% by weight of said adhesive matrix.

28. The method of claim 27 wherein said acid is selected from the group comprising L-tartaric acid, salicylic acid, hydrochloric acid and mixtures thereof.

29. The method of claim 28 wherein said acid is added to said adhesive matrix formulation in a acid/nicotine molar ratio of from about 1:2 to 2:1.

30. A method for the treatment of nicotine addiction by the transdermal administration of nicotine in an amount sufficient to reduce the craving therefore by the topical application of the delivery system of claims 1 or 15 to an addict.

31. A nicotine patch for the cure of an addiction thereto comprising the transdermal delivery system of claims 1 or 15.

32. A method for the preparation of a transdermal delivery system for the subcutaneous administration of nicotine in an amount sufficient to reduce the craving therefore comprising:
   a) preparing an adhesive matrix consisting of an acrylic polymer adhesive, nicotine base, a stabilizer, an emulsion thickener and an acid;
   b) laminating said adhesive matrix onto an inert impermeable film backing;
   c) heating said adhesive matrix laminate at a sufficient temperature and time to evaporate any solvent contained therein; and
   d) laminating a removable release liner over the exposed surface of the dried acrylic adhesive/nicotine base matrix.

33. The method of claim 33 wherein said release liner is silicone- or fluorocarbon-based.

* * * * *